(12) United States Patent
Shahinpoor et al.

(10) Patent No.: US 7,276,090 B2
(45) Date of Patent: Oct. 2, 2007

(54) METHOD OF FABRICATING A DRY ELECTRO-ACTIVE POLYMERIC SYNTHETIC MUSCLE

(75) Inventors: Mohsen Shahinpoor, Albuquerque, NM (US); Kwang J. Kim, Albuquerque, NM (US)

(73) Assignee: Environmental Robots, Inc., Albuquerque, NM (US)

( * ) Notice: Subject to any disclaimer, the term of this patent is extended or adjusted under 35 U.S.C. 154(b) by 594 days.

(21) Appl. No.: 09/899,874

(22) Filed: Jul. 5, 2001

(65) Prior Publication Data

US 2002/0050454 A1 May 2, 2002

Related U.S. Application Data

(60) Provisional application No. 60/217,210, filed on Jul. 10, 2000.

(51) Int. Cl.
*H01G 9/00* (2006.01)

(52) U.S. Cl. ............... 29/25.03; 29/831; 29/846
(58) Field of Classification Search ........... 29/25.03, 29/831, 846; 438/3.22, 3, 22; 977/DIG. 1
See application file for complete search history.

(56) References Cited

U.S. PATENT DOCUMENTS

| | | | | |
|---|---|---|---|---|
| 4,087,376 A | * | 5/1978 | Foris et al. | 427/213.34 |
| 4,338,000 A | * | 7/1982 | Kamimori et al. | 359/275 |
| 5,054,323 A | * | 10/1991 | Hubbard et al. | 73/754 |
| 5,060,527 A | * | 10/1991 | Burgess | 73/862.68 |
| 5,424,907 A | * | 6/1995 | Kojima et al. | 361/532 |
| 5,445,856 A | * | 8/1995 | Chaloner-Gill | 428/35.9 |
| 5,638,205 A | * | 6/1997 | Meisel et al. | 359/350 |
| 5,750,272 A | * | 5/1998 | Jardine | 428/686 |

OTHER PUBLICATIONS

Controlled Folding of Micrometer-Size Structures E. Smela, O. Inganas, I. Lundstrom, Science 268, 1735 (1995).
Electrochemomechanical properties from a bilayer; polypyrrole/non-conducting and flexible material—artificial muscle. T.F. Otero, J. Rodreguez, E. Angulo, C. Santamaria, J. Electroanal Chem. 341, 369 (1992).
Performance and work capacity of a polypyrrole conducting polymer linear actuator, A. Della Santa, D. De Rossi, A. Mazzoldi, Synthetic Metals, 90, 93 (1997).
Mechanism of electromechanical actuation in polypyrrole M.R. Gandhi, P. Murray, G.M. Spinks, G.G. Wallace, Snyth. Met. 73, 247 (1995).

(Continued)

*Primary Examiner*—Carl J. Arbes
*Assistant Examiner*—Tai Nguyen
(74) *Attorney, Agent, or Firm*—Dennis F. Armijo

(57) ABSTRACT

New polymeric materials and their fabrication methods that are electrically active in terms of sensing and actuation are invented. These materials are comprised of solid-state ion-conducting materials such as polyethylene oxide (PEO) and its derivatives or imbedded in a family of mixed polymer systems such as polydivinylbenzene (DVB) and polystyrene polymers. Such materials suitably electroded with conductive materials such as gold, platinum and silver exhibit large deformation (both two and three dimensionally) under low electric fields of 10's V/mm. Conversely, if these materials are deformed, they produce 10's of mV/mm electric fields that can be used as means of sensing or electromechanical powering devices for batteries. The method of fabricating the new polymeric materials comprises the steps of providing a polyelectrolyte material, mixing the polyelectrolyte material with a conductive material and affixing at least two electrodes to the mixed polyelectrolyte material and conductive material.

12 Claims, 22 Drawing Sheets

OTHER PUBLICATIONS

Conductive polymer based structures for a steerable catheter A. Mazzoldi, D. DeRossi, Proceedings of SPIE–Electroactive Polymer Actuators and Devices (EAPAD) 3987, 273 (2000).

Giant Electrostriction and Relaxor Ferroelectric Behavior in Electron–Irradiated Poly(vinylidene flouride–trifluoroethylene) Copolymer, Q.M. Shang, V. Bharti, X. Zhoa, Science 280, 2101 (1998).

Ferroelectric Polymers, A.J. Lovinger, Science 220, 1115 (1983).

Ionic Polymer–metal composites (IPMC) as Biomimetic Sensors, Actuators & Artificial Muscles—A Review, M. Shahinpoor, Y. Bar–Cohen, J.O. Simpson, J. Smith, Smart Mater. Struct. 7, 15 (1998).

Mechanoelectric efforts in ionic gels, P.G. De Gennes, K. Okumura, M. Shahinpoor, K.J. Kim, Europhysics Letters 50, 513 (2000).

Bending of Polyelectrolyte Membrane–Platinum Composites by Electric Stimuli I. Response Characteristics to Various Waveforms, K. Asaka K. Oguro, Y. Nishimura, M. Mizuhata, H. Takenaka, Polym. J. 27, 436 (1995).

Ionic Polymeric Gels, R. Hamden, C. Kent, S. Shafer, Nature 206, 1149 (1965).

Collapse of Gels in an Electric Field, T. Tanaka, I. Nishio, S. Sun, S. Ueno–Nishio, Science 218, 467 (1982).

A polymer gel with electrically driven motility, Y. Osada, H. Okuzaki, H. Hori, Nature 355, 242 (1992).

Deformation of Ionic Polymer Gels by Electric Fields, M. Doi, M. Matsumoto, Y. Hirose, Macromolecules 25, 5504 (1992).

* cited by examiner

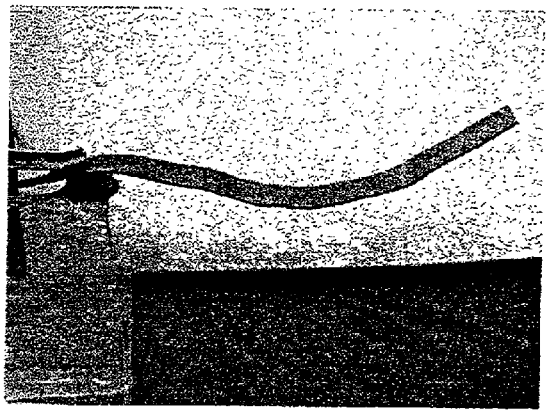 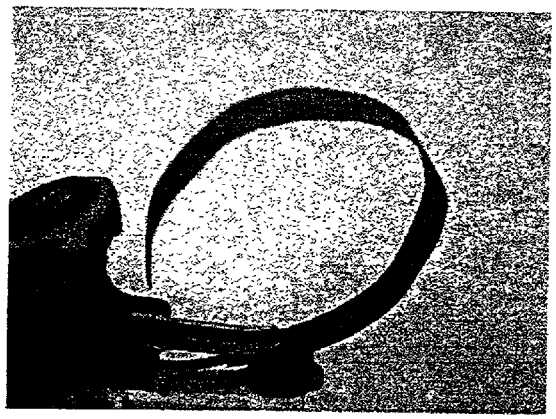
Fig. 14a                    Fig. 14b

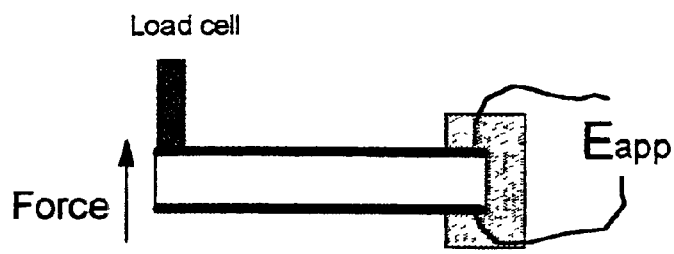
Fig. 17a
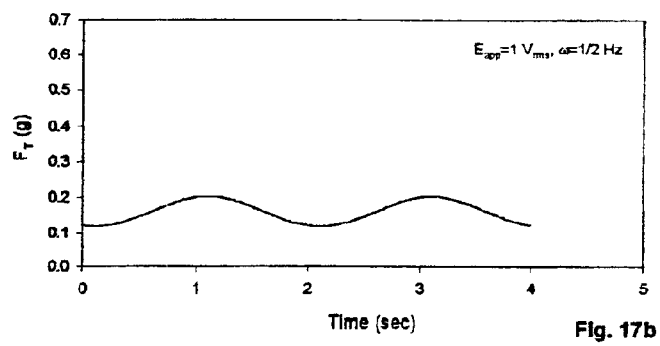
Fig. 17b
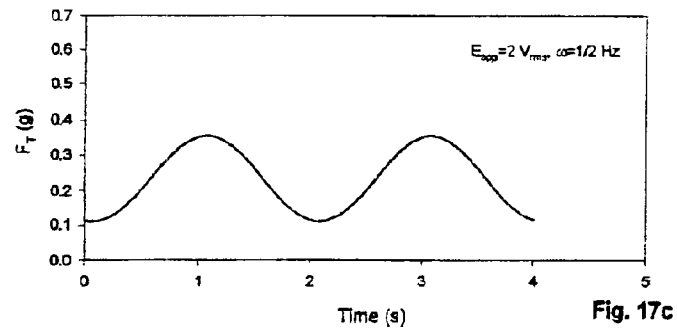
Fig. 17c
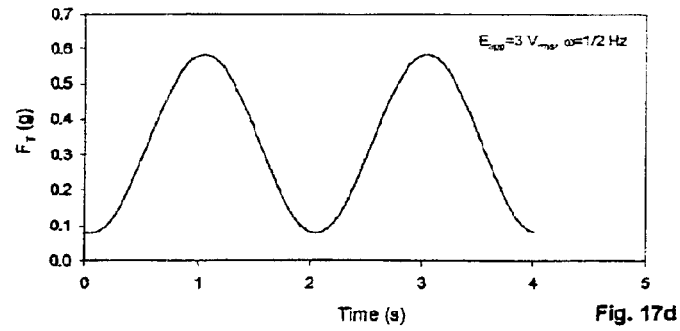
Fig. 17d
Fig. 17

METHOD OF FABRICATING A DRY ELECTRO-ACTIVE POLYMERIC SYNTHETIC MUSCLE

CROSS-REFERENCE TO RELATED APPLICATIONS

This application is based on U.S. Provisional Application Ser. No. 60/217,210 entitled "Solid-state polymeric sensors and actuators" filed on Jul. 10, 2000, the teachings of which are incorporated herein by reference.

BACKGROUND OF THE INVENTION

1. Field of the Invention (Technical Field)

The present invention relates to sensors and actuators, and more particularly to polymeric materials and the fabrication processes for solid state polymeric sensors and actuators.

2. Background Art

Polymeric devices that can directly convert electric energy to mechanical energy (electromechanical effects) have attracted a great deal of attention in recent years. The definite advantages of such polymeric devices originate from their soft mechanical properties (inherently polymeric behavior) that have a significant potential to mimic various biological situations necessary to enhance human activities and/or serve as special industrial actuators. A number of prior art materials in this category recognized so far include: i) conducting polymers, E. Smela, O. Inganas, I. Lundstrom, Science 268, 1735 (1995); T. F. Otero, J. Rodriguez, E. Angulo, C. Santamaria, J. Electroanal Chem. 341, 369 (1992); A. Della Santa, D. De Rossi, A. Mazzoldi, Synthetic metals, 90, 93 (1997); M. R. Gandhi, P. Murray, G. M. Spinks, G. G. Wallace, Synth. Met. 73, 247 (1995); A. Mazzoldi, D. De Rossi, Proceedings of SPIE-Electroactive Polymer Actuators and Devices (EAPAD) 3987, 273 (2000); ii) ferroelectric polymers Q. M. Zhang, V. Bharti, X. Zhao, Science 280, 2101 (1998); J. Lovinger, Science 220, 1115 (1983); iii) ionic polymer metal composites M. Shahinpoor, Y. Bar-Cohen, J. O. Simpson, J. Smith, Smart Mater. Struct. 7, 15 (1998); P. G. De Gennes, K. Okumura, M. Shahinpoor, K. J. Kim, Europhysics Letters 50, 513 (2000); K. Asaka, K. Oguro, Y. Nishimura, M. Mizuhata, H. Takenaka, Polym. J. 27, 436 (1995); and iv) ionic polymeric gels R. Hamden, C. Kent, S. Shafer, Nature 206, 1149 (1965); T. Tanaka, I. Nishio, S. Sun, S. Ueno-Nishio, Science 218, 467 (1982); Y. Osada, H. Okuzaki, H. Hori, Nature 355, 242 (1992); M. Doi, M. Matsumoto, Y. Hirose, Macromolecules 25, 5504 (1992).

Conducting polymers can become electromechanically active via electrochemical dopant intercalation in the redox material. Although the predicted force/power generation capability of conducting polymers are high, development efforts are hampered due to rate-limiting interfacial dopant diffusion and, therefore, cost their lifetime and thermodynamic efficiency. Also, its operation in dry environments is possible but not effective to create useful strain for appropriate engineering applications. Ferroelectric materials such as poly(vinyliedene fluoride-trifluoroethylene, PVDF-TrFE) copolymer are recently recognized as giant electrostriction and relaxor and operational in dry environments but require very high electric field (>10 kV/mm) for an appropriate range of actuation capabilities to attract engineering applications. Ionic polymer metal composites in a form of a strip show a large bending capability under a small electric field (<10 V/mm) along with considerable forces and fast responses. However, the operation of these devices is effective only in wet climates, therefore, the engineering applications are limited to wet environments. Ionic polymer gels, such as PVA fibers and polyacrylamide, can also show electromechanical behavior. Ionic currents create local ion exchanges so as to alter the osmotic pressure in polymer gels, i.e., Donnon exchange. However, such ionic polymer gels suffer from their weak mechanical strength and consequent microfractures upon large deformations and result in short life span materials.

The present polymer solid-state actuators overcome many inherent problems that other state-of-the-art polymer actuators have, such as rate limiting dopant intercalation of conducting polymers, high voltage requirement of ferroelectric polymers, favorable wet conditions of ionic polymer metal composites, and poor mechanical properties of ionic polymeric gels. Therefore, the disclosed solid-state polymer actuators and sensors have tremendous potential for use in biomimetic/medical, industrial, and domestic applications than the present prior art polymer materials.

SUMMARY OF THE INVENTION (DISCLOSURE OF THE INVENTION)

In accordance with the present invention, there is provided an method for fabricating a dry electro-active polymeric synthetic muscle comprising the steps of providing a polyelectrolyte material, mixing the polyelectrolyte material with a conductive material and affixing at least two electrodes to the mixed polyelectrolyte material and conductive material. The preferred step of mixing comprises mixing a soluble polyelectrolyte material with an ion conducting powder and drying the mixed polyelectrolyte material with the conductive material. The step of mixing also can comprise combining a dry polyelectrolyte material with a dry conductive material and applying heat to the combined materials. The step of mixing can also comprise combining a dry polyelectrolyte material with a dry conductive material and applying pressure to the combined materials. The preferred step of affixing at least two electrodes comprises penetrating the at least two electrodes into the mixed polyelectrolyte material and conductive material. The step of penetrating the at least two electrodes into the mixed polyelectrolyte material and conductive material comprises heating the penetrated at least two electrodes and the mixed polyelectrolyte material and conductive material. The step of penetrating the at least two electrodes into the mixed polyelectrolyte material and conductive material can also comprise pressurizing the penetrated at least two electrodes and the mixed polyelectrolyte material and conductive material. The step of affixing at least two electrodes can also comprise physical loading and interlocking primary electrically conducting particles with smaller electrically conducting particles within the polyelectrolyte material. The preferred polyelectrolyte material comprises a member from the group consisting of polyethylene oxide, polyethylene succinate, polypropiolactone, polyethylene adipate, polypropylene oxide, polymethacrylic acid, polyacrylonitrile, polybis-methoxyethoxyethoxy phosphazene and polyvinylidene fluoride. The preferred synthetic muscle comprises a sensing device, a transducing device or an actuating device.

The preferred dry electro-active polymeric synthetic muscle comprises a polyelectrolyte material mixed with a conductive material and at least two electrodes affixed to said mixed polyelectrolyte material and conductive material. The at least two electrodes preferably penetrate into the mixed polyelectrolyte material and conductive material. The polyelectrolyte material comprises a member from the group consisting of polyethylene oxide, polyethylene succinate, polypropiolactone, polyethylene adipate, polypropylene oxide, polymethacrylic acid, polyacrylonitrile, polybismethoxyethoxyethoxy phosphazene and polyvinylidene fluoride. The at least two electrodes comprise a member from the group consisting of screen mesh, conducting polymers, carbon-nanotubes, porous materials, metals, metal alloys and conducting powders. The synthetic muscle preferably comprises a sensor, a transducer or an actuator.

A primary object of the present invention is to provide a family of multi-functional ionic polymers capable of sensing, transduction, and actuating with a broad range of applications.

Yet another object of the present invention is to provide such multi-functional materials with built-in sensing and feed back control capabilities.

Yet another object of the present invention is to provide dry, rather than wet or moist or in a chemical solution, solid sate biomimetic sensors, transducers, and actuators that can be integrated with electronics and data acquisition systems and robotics applications.

Yet another object of the present invention is to provide actuators, sensors, and actuators/sensors that are capable of undergoing spectacular bending or flexing displacement.

A primary advantage of the present invention is that it provides sensors, transducers, and actuators for actuating and/or sensing displacement, rotation, force, torque, acceleration, frequency, concentration, charge, and degradation.

Another advantage of the present invention is that it provides sensors, transducers, and low voltage actuators that operate in a dry, non-moist environment which has been a necessary environment for actuation of all previously claimed polymeric actuators or sensors.

Another advantage of the present invention is to provide actuators, sensors, and actuators/sensors that are capable of simultaneously sense any change in their configuration or dynamics and yet be capable of changing their shape or dynamics by applying an electric field of the order of few volts per mm.

Another object of this invention is that it provides a family of multi-functional materials with built-in feedback sensing, actuation, and transduction capabilities.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIGS. 14a and 14b pictorially show the bending capabilities of the preferred polymer solid-state actuator.

FIG. 17a is a diagram showing the force measurement setup for the preferred manufactured polymer solid-state actuator.

FIGS. 17b, 17c, and 17d are graphs of the force responses for the set-up of FIG. 17a at sinusoidal input potentials of 1, 2, and 3 volts, respectively.

DESCRIPTION OF THE PREFERRED EMBODIMENTS (BEST MODES FOR CARRYING OUT THE INVENTION)

Figures 1A, 1B:
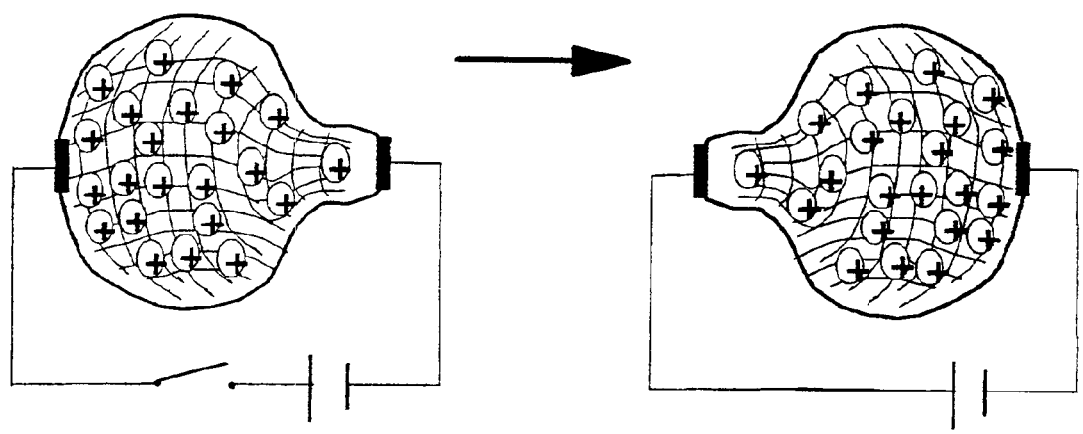
FIGS. 1a and 1b demonstrate the principle of electrically controllable polymer components and bodies.
Figure 2:
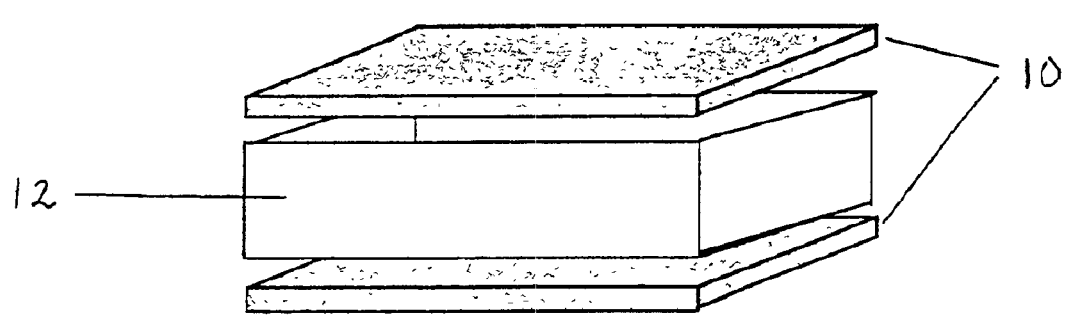
FIG. 2 is a perspective view showing the two dimensional fabrication principle.

Novel fabrication methods and new materials have been developed for preparing electroactive polymers as the active two and three-dimensional components and bodies in electromechanical or mechano-electric devices that can be used for actuators and sensors and artificial muscles. FIGS. 1a and 1b demonstrate the principle of electrically three dimensional polymer components and bodies for actuation and shape changes. FIG. 1a represents the principle of the invention with no power applied and FIG. 1b represents the principle of the invention with an electrical field applied. FIG. 2 similarly shows the two dimensional fabrication principle with ion conductive materials 10 sandwiching electroactive polymer 12. The electromechanical devices in three-dimensional configurations, FIGS. 1a and 1b, and the two dimensional structure, FIG. 2, generate substantial conformational changes with minimum input of electric potential. It is also possible to vary surface properties of such devices upon changing electric fields.

In the following Table 1, identified materials that can be used as the embodiment of the invented devices are listed. The provided list of materials are the main body of the solid-state polymeric sensors, transducers, and actuators. These materials are processed to form any shape via solution casting or precursor conversion processes that will be described later in this section. The underlying principle of using these materials arises from their high electric conductivity in solid-state applications. Effective combination of materials is to enhance ion transport within ion conducting medium incorporating additives and, at the same time, improving mechanical strength by using structural containment or housing materials.

TABLE 1

| | |
|---|---|
| Ion conducting medium | Poly(ethylene oxide) [PEO] and its derivatives including oligomeric PEO, poly(ethylene succinate), poly(propiolactone), and poly(ethylene adipate); Poly(propylene oxide) [PPO] and its derivatives (linear, network, and block); Poly(methacrylic acid) [PMMA]; Polyacrylonitrile [PAN]; Poly[bis-(methoxyethoxyethoxy)phosphazene] [MEEP]; Poly(vinylidene fluoride) [PVDF]; |
| Additives | Propylene carbonate; Ethylene carbonate; Polyethylene glycol; Acetonitrile; Butyrolacetone; Dimethyl formamide [DMF]; Water; |
| Structural containment or housing materials | Perfluoropolyelectrolytes in the form of sulphonic acid or carboxylic acid; Poly(methacrylic acid) [PMMA]; polydivinylbenzene [DVB]; polystyrene and its derivatives; |

Figure 3:
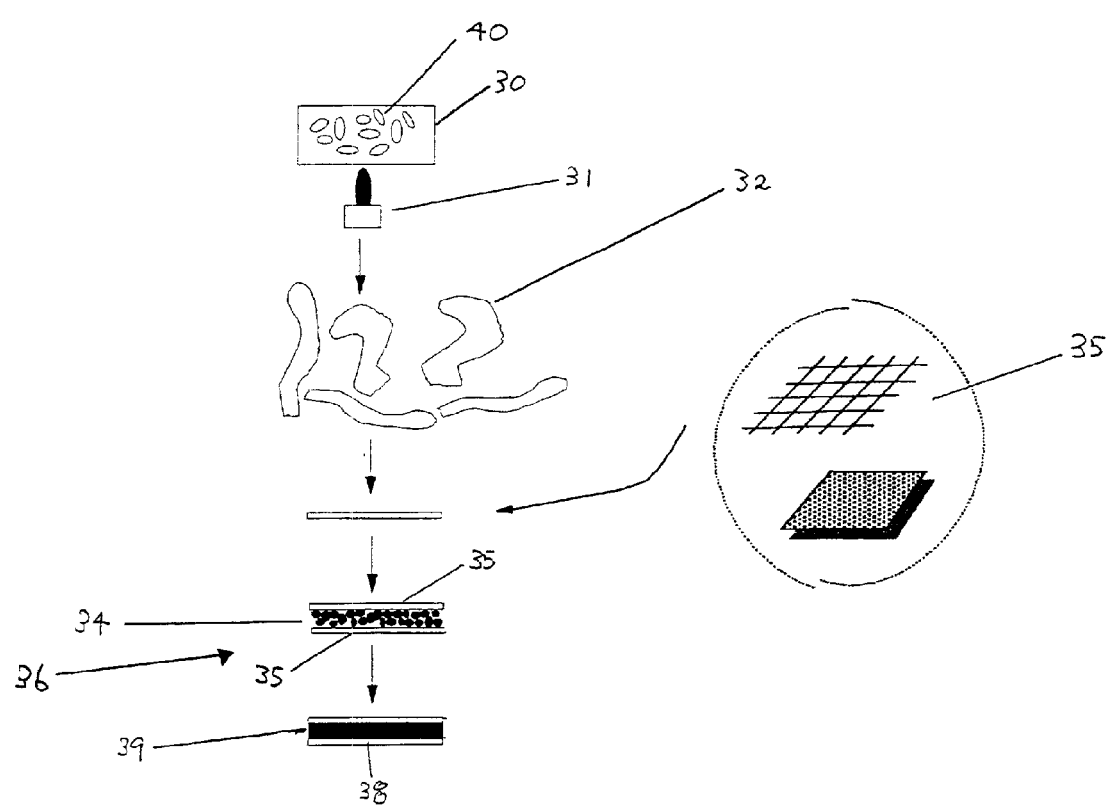
FIG. 3 shows the preferred process for fabricating a recompressed expanded graphite electrode made by the preformer melting process.

A recompressed expanded graphite electrode made by the preformer melting process is shown in FIG. 3. The principle of such a process is to incorporate thermoplastic materials to form three dimensional structures and subsequently convert them into electroactive forms. As can be seen in FIG. 3, initially, expandable graphite 30 contains impurities 40 such as water, sulfur, and metal oxides. By applying heat 31 in air (usually 300<T<1,000° C.), the graphite 32 expands. The lamellar structure of graphite powder is thereby transformed into a worm-like structure by the thermal expansion, while the impurities 40 are removed by heating. Typical volume expansion is equivalent to 30–100 fold giving an apparent density in the range of 5–12 kg/m$^3$. Expanded graphite 32 is recompressed 34 into thin electrodes 35 (approximately 10–300 µm thickness) having an approximate electric resistance of 1–10 ohm/square (based upon four-probe method). Electrodes 35 can be screen mesh, conducting polymers, carbon-nanotubes, porous material, metal, metal alloys, conducting powders. Preformer 36 (such as sulfonyl fluoride vinyl ether/tetrafluoroethylene) is placed between two recompressed expanded graphite electrodes 35 and undergoes the thermal process. During the thermal expansion process, preformer 36 melts by heat and migrates into recompressed expanded graphite electrode 35 under applied pressure (or the termocapillary effect), and is impregnated within the graphite 38. Later, the preformer 36 is converted to electroactive polymers 39 via base hydrolysis using an aqueous solution that includes dimethylsulfoxide and KOH (NaOH or LiOH).

Figure 4:
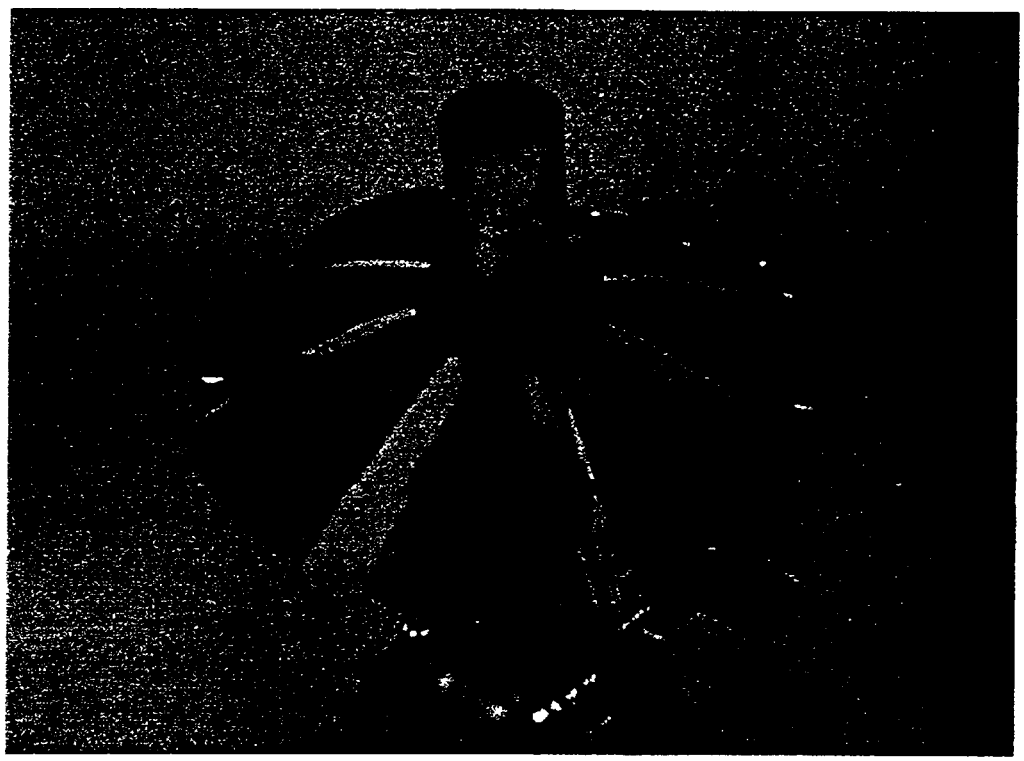
FIG. 4 shows an example of the material fabricated based upon the method of FIG. 3.

Note that the expanded graphite electrode 35 used in this example can be replaced by any means of conducting medium such as metals, metal alloys, conducting polymers, carbon-nanotubes, conductive screen meshes, conductive porous materials, and others. In addition, chemical reducing techniques to form a finely-divided metal layer on top of the active polymer can be adopted. The underlining principle of this example is to incorporate thermoplastic preformer to form any three dimensional shapes initially and, later, to convert them into active material via base hydrolysis. Therefore, any desired shapes of active components and bodies can be formed. FIG. 4 shows an example of the material fabricated based upon this method and demonstrates that the material has enough strength to lift more than 8 U.S. quarters in a cantilever configuration. The diameter of this material is approximately 10.5 cm. The electrode is centered. The middle and bottom photographs show this material in action without applying load and with a load. Note that platinum was composited initially and gold was plated later. The cation is Li$^+$.

Figure 5:
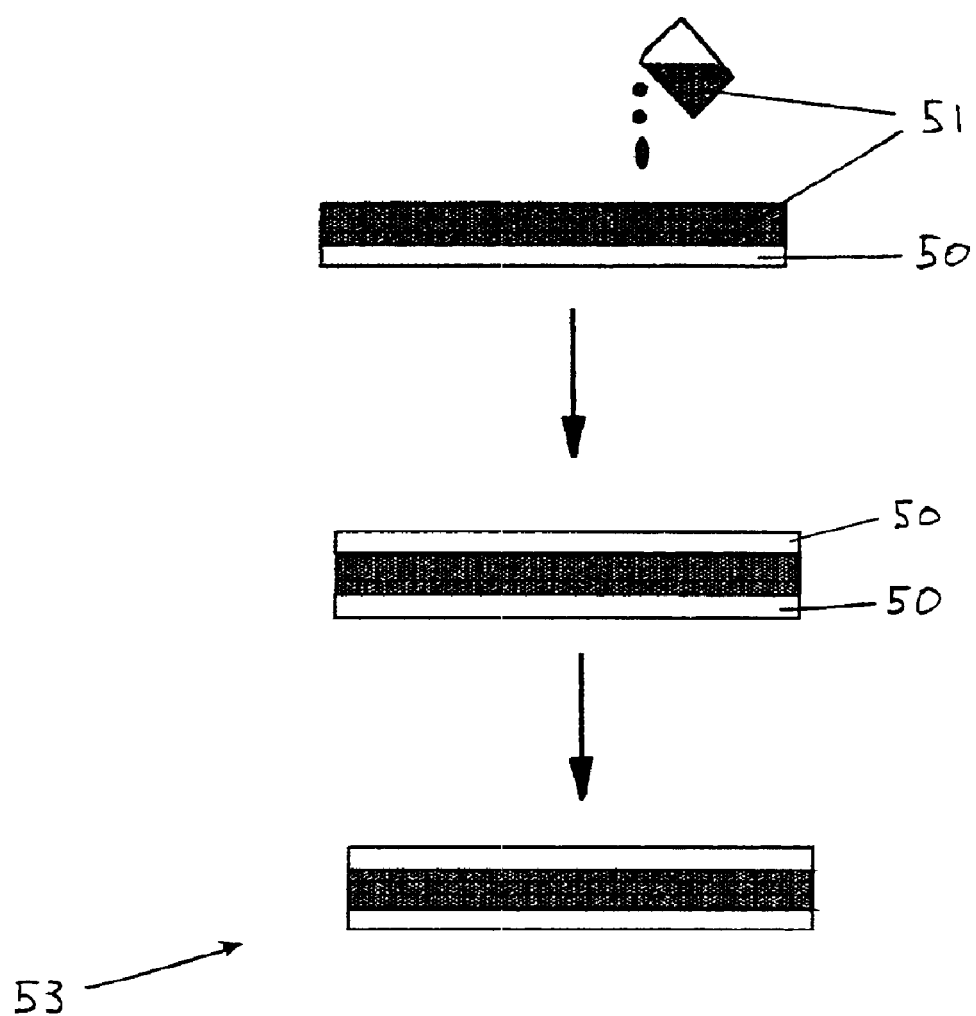
FIG. 5 depicts the preferred method of fabricating a recompressed expanded graphite electrode made by the electroactive polymer solutions (recasting technique).

A recompressed expanded graphite electrode 50 made by an electroactive polymer solution 51 (recasting technique) is described in FIG. 5. First, two identical recompressed expanded graphite electrodes 50 and 50' are prepared by the method described previously in FIG. 3. Second, electrode 50 is horizontally placed and the electroactive polymer solution 51 is poured on the top 52 of the recompressed expanded graphite electrode 50. Usually, the electroactive polymer 51 can be dissolved in a mixture of a number of solvents (not shown). Therefore, the repeated evaporation of solvents is necessary to obtain a desirable thickness of the electroactive polymer layer. In practice, a layer by layer approach to obtain any desirable shapes is effective. Third, another recompressed expanded graphite electrode 50' is placed on the top of the electroactive polymer layer 51. As a final step, the recompressed expanded graphite electrode assembly 53 made by the electroactive polymer solution undergoes the thermal process for a curing. This process is necessary in a sense that a desirable level of crystallinity can be achieved. Again, any means of conducting medium as mentioned above can be used as the electroding material.

Figure 6:
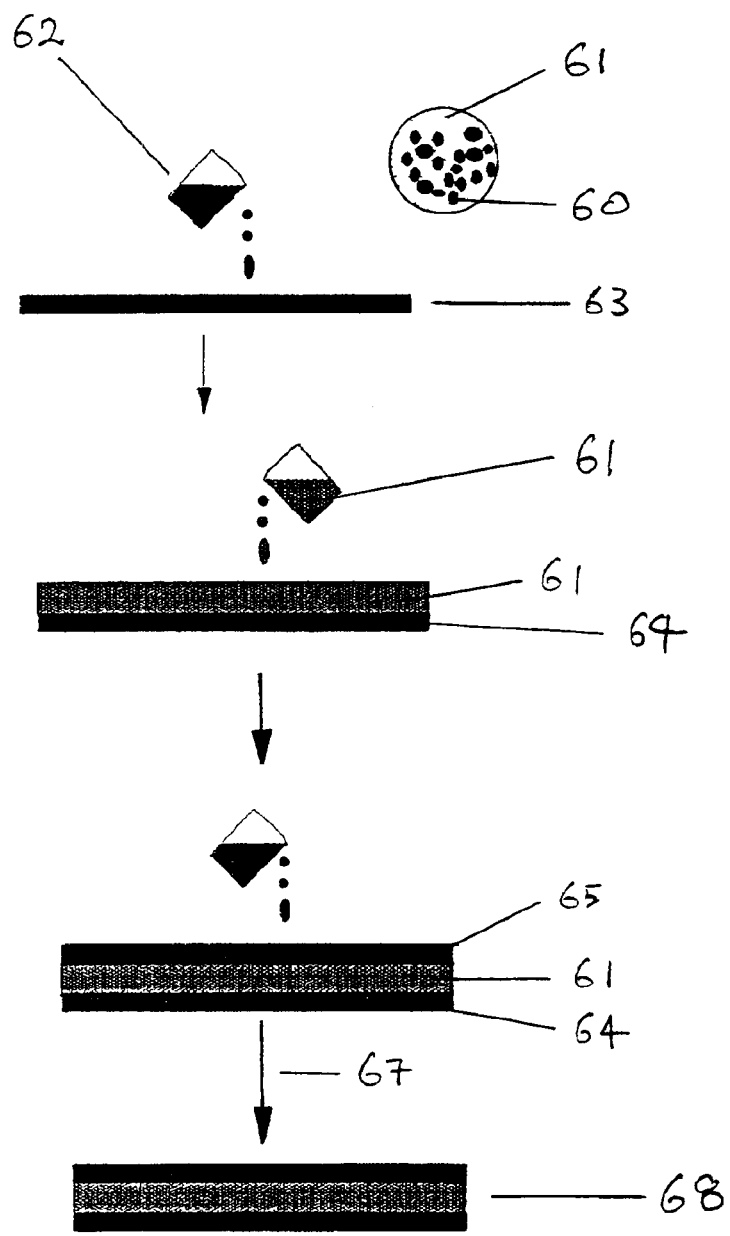
FIG. 6 depicts the preferred method of fabricating an ion conducting powder coated electrode.

An ion conducting powder coated electrode process diagram is illustrated in FIG. 6. First, the ion conducting powder 60 (i.e., Carbon, graphites, carbon nanotubes, Silver, Platinum, Palladium, Gold, Copper, and any other conducting powders) is mixed with the electroactive polymer solution 61. The ion conductive powder 60 is fine and uniformly dispersed within the electroactive polymer solution 61 to make a powder/solution mix 62 and is poured to form a first thin layer 63. After a formation of a thin layer 63 the powder/solution mix 62 undergoes a drying process of solvents and, therefore, the residual consists of the ion conducting powder dispersed within the solid polymer 64. Second, additional electroactive polymer solution 61

(without the powder) is added on the top of the layer of the ion conducting powder dispersed within the solid polymer 64 and dried. This is repeated until the desired thickness is obtained (not shown). Next, an additional layer of the ion conducting powder dispersed within the solid polymer 65 is formed by the same method described above. As a final step, the ion conducting powder-coated electrode 66 is cured 67 under the elevated temperature based upon a similar method described in FIG. 5, to form a ion conducting powder coated electrode 68.

Figure 7:
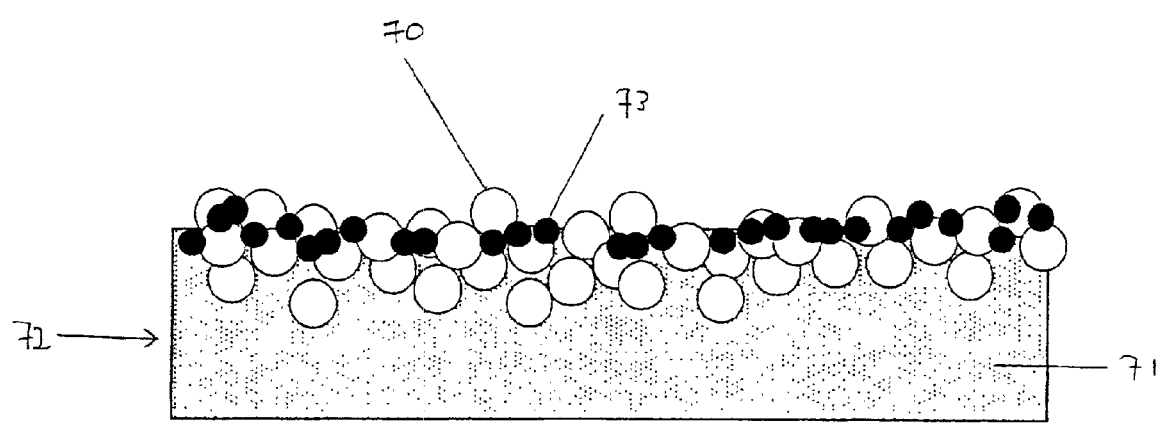
FIG. 7 is a schematic process illustration of the physical loading of conductive phases and subsequent interlocking for making electrodes.

Physical loading of conductive phases and subsequent interlocking (PLCP-SI) for making electrodes is shown in FIG. 7. The principal idea of processing the PLCP-SI is to first load conductive primary powders 70 (or phases) into the polymer network 71 forming a dispersed layer 72 which can function as a major conductive-passage and, subsequently, to interlock primary particles 73 within the polymer network 71 with smaller particles 73 via a chemical process. So, the primary 70 and smaller-interlocking particles 73 can be secured within the polymer network 71. Furthermore, an electroplating (not shown) can be applied to integrate the entire conductive phase in tack serving as an effective electrode. Effective materials can be used for this final in-tack process include gold, palladium, silver, and any other conducting metal that can be formed via electroplating. The process includes the following steps:

1. A silver-based spherical powder (MOx-Doped Ag; Superior MicroPowders EM10500X-003A; $D_{10}$<0.8 μm, $D_{50}$<1.5 μm, $D_{90}$<2.5 μm; $A_{sur}$<6 m$^2$/g) is dispersed in isopropyl alcohol (99%). Using a standard air-brush (VEGA), the powder is spayed onto the backing material (i.e. filter paper).

2. Wait until isopropyl alcohol completely evaporates.

3. The ionic polymer is first surface-treated with the sandpaper (#400). The standard size of the polymer sample is about 1×1".

4. The ionic polymer is placed between the backing materials facing the powder-coated side.

5. Pressing is carried out at about 2 ton using a temperature controlled hot-press (RAMCO, 50 ton capacity) at 120–130° C. for a duration of 15 minutes.

6. Repeat the process 1–5, three times. Usually, low electric surface-resistance is obtained (R<1Ω/square by the four probe).

7. The preferred interlocking process is to impregnate small novel metal particles (i.e. platinum or palladium, $D_p$~50 nm) between the primary particles so as to immobilize them within the ionic polymer). This interlocking process is to introduce metallic ions such as [Pt(NH$_3$)$^{2+}$] into the ionic polymer initially and, later, reduce them to a metallic state.

8. As a final step, a conductive metallic layer (i.e. gold or palladium) is simply electroplated on the top of the layer.

Figure 8:
FIG. 8 is a SEM micrograph of the electrode fabricated using the method of FIG. 7.

In FIG. 8, a SEM micrograph of the electrode fabricated using the method of FIG. 7 is provided.

Figure 9:
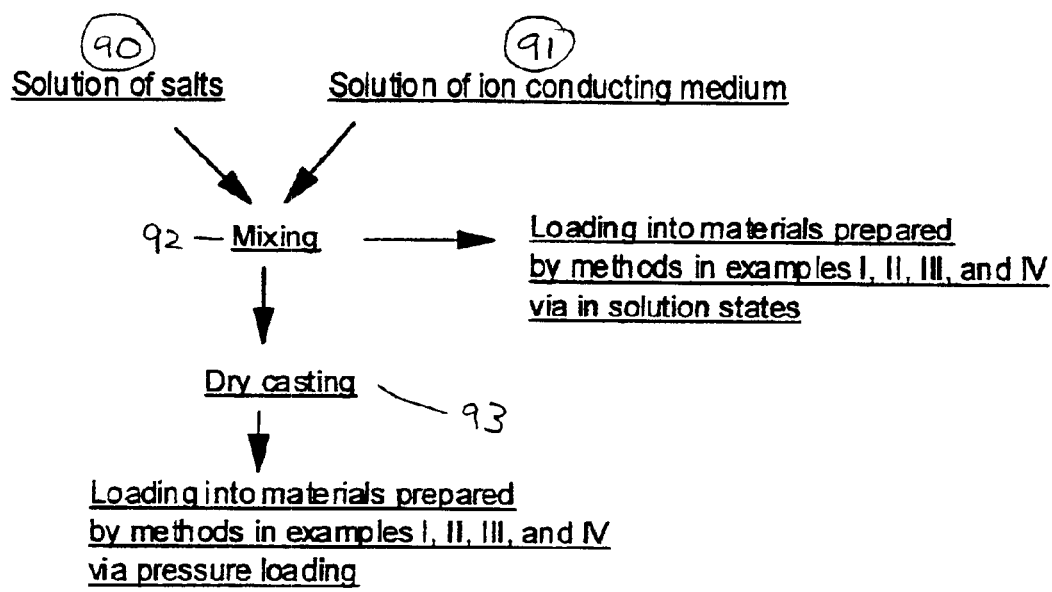
FIG. 9 depicts the preferred method for preparation of an electroactive polymer solid-state actuator and sensor material.

Preparation of the electroactive polymer solid-state actuator and sensor materials is shown in FIG. 9. The preparation process involves the dissolution of each salts 90 and conjugated ionconducting medium in a suitable solvent 91 (e.g. acetonitrile, water), the mixing 92 of them in a single solution and slow evaporation or dry casting 93 of the solvent. This casting procedure 93 is effective and simple since it results in materials of various desired forms and of different thickness and even various shapes. Electroding materials can be added as previously described in FIG. 2. Such casting procedure illustrated in FIG. 9 gives polymeric materials, which are thin or thick, flexible, processable, and ionically conductive. Making the material electroactive involves appropriate processes including solution state loading or pressure loading.

Figure 10:
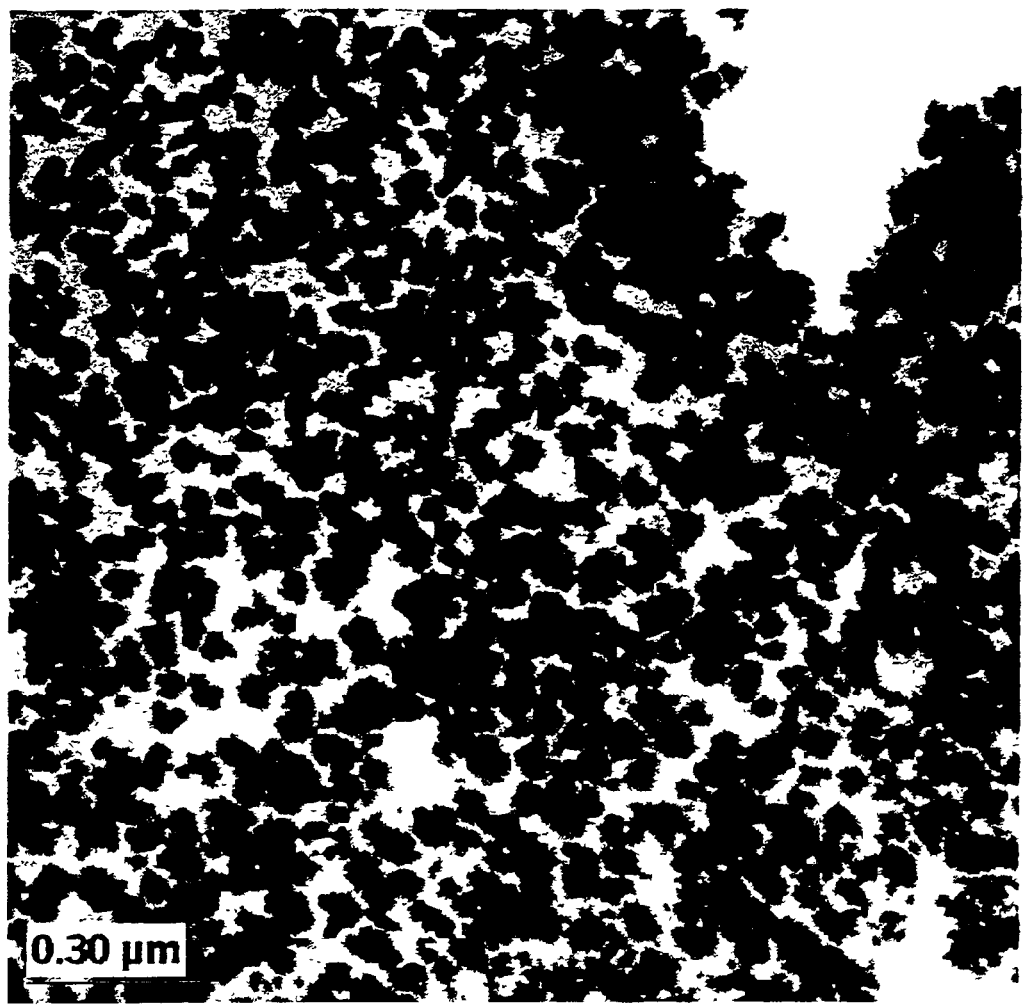
FIG. 10 shows a TEM micrograph that depicts the platinum particles within the material

One key engineering challenge for achieving high force actuation is to reduce or eliminate the PEO/PEG leakage out of the surface electrode (if it is made of finely divided platinum particles) such that PEO/PEG transport within the material can be more effectively utilized for actuation. One can realize that there is a significant potential to control the particle forming process (in term of conductive particle penetration, size, and distribution). To do so could be achieved by introducing effective dispersing agents (additives) during the chemical reduction process. One can anticipate that the effective additives should enhance to disperse platinum particles within the ion material and reduce coagulation. As a result, a better platinum particle penetration into the material with a somewhat smaller particle size with good distribution could be obtained. FIG. 10 shows a TEM micrograph that depicts the platinum particles within the material. Note the well distributed particles.

Figure 11:
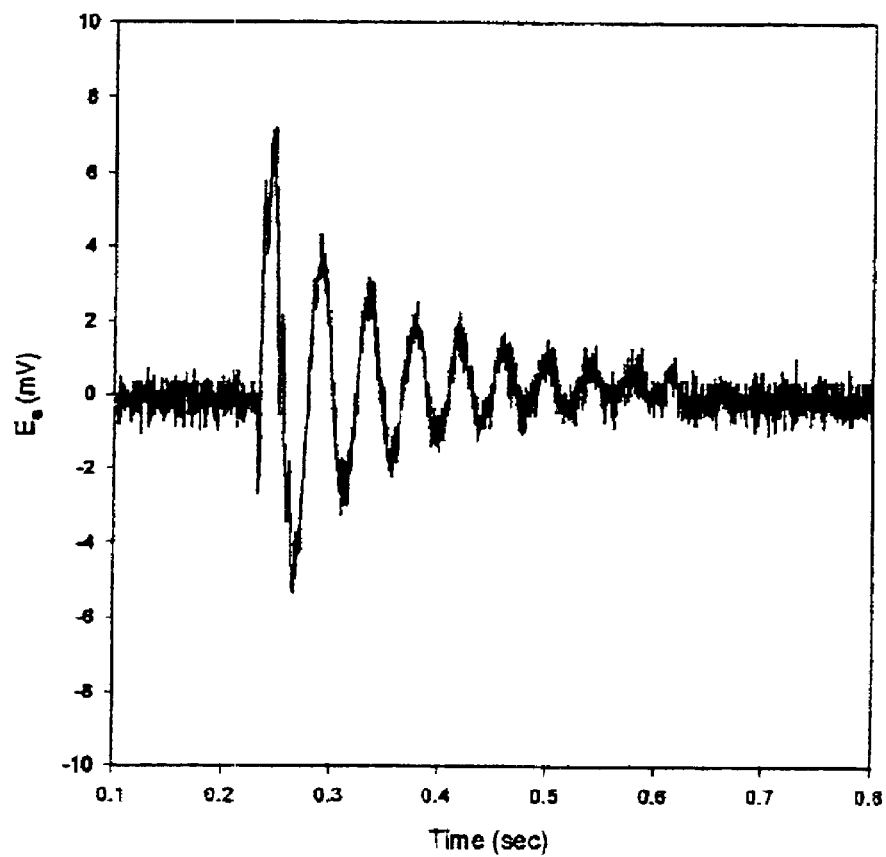
FIG. 11 is a graph showing the dynamic sensing response in output voltage of a solid state polymer.
Figure 12:
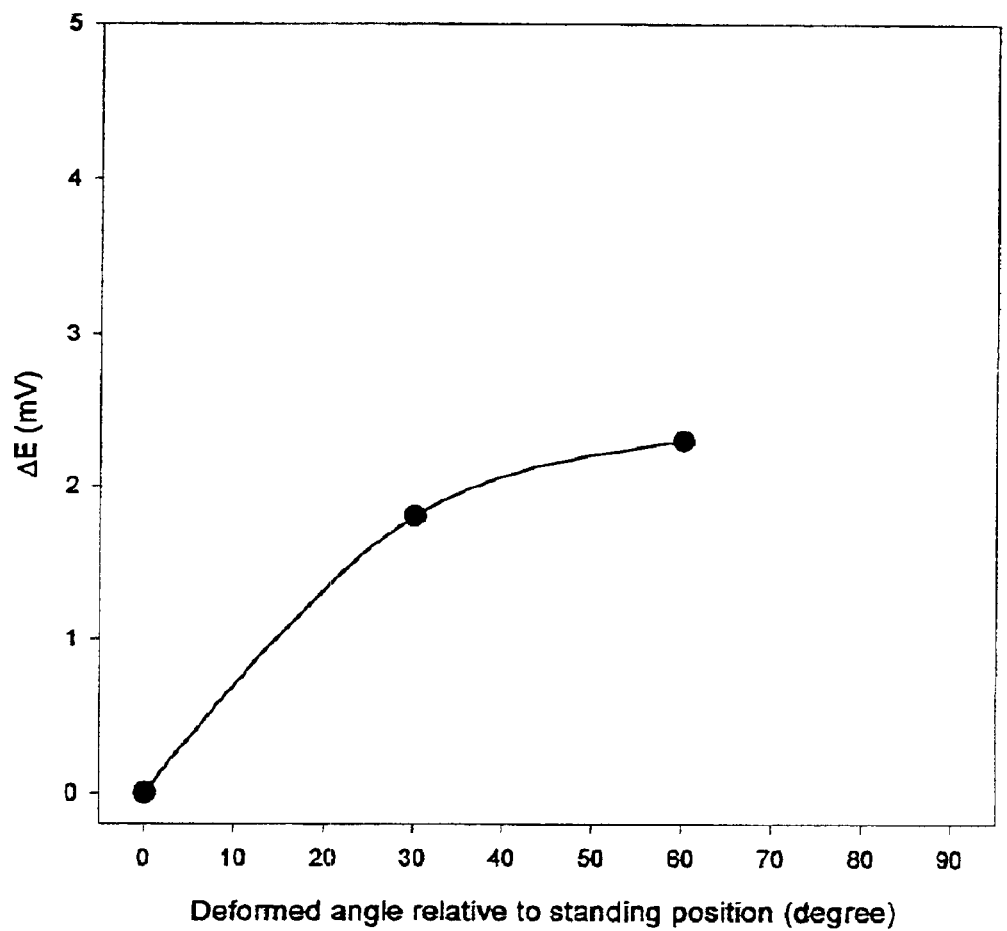
FIG. 12 is a graph showing sensing data in terms of produced voltages, $\Delta E$ vs. displacement of a sample sensor.

The response times are short and the efficiency of these devices is high. Also, such devices can produce sensible electric signals via endo-ionic mobility phenomena as shown in FIG. 11. FIG. 11 shows the dynamic sensing response of an output voltage of a polymer solid state sensor (50.8×6.1 mm) subjected to a dynamic impact lading in a cantilever configuration. Furthermore, the present invention can be used as smart sensors concerning displacement and the output voltages as shown in FIG. 12. FIG. 12 is a graph showing sensing data in terms of produced voltages, ΔE vs. displacement. Note, that in this graph that the displacement, the cantalever configuration, is shown in terms of deformed angles relative to standing position in degree. The dimension of the sample sensor is 5×0.12 mm. By the method of the present invention, the active component is fabricated by laminating and/or compositing highly conductive materials (these serve as effective electrodes and capacitors) onto external surface of, and into electroactive polymers. It should be pointed out that these fabrication techniques herein focus on both two and three-dimensional fabrications of artificial muscles, actuators, and sensors and associated materials. Obviously, they can be easily applicable for one dimensional devices as well.

Figure 13A:
FIG. 13a is a schematic rendering of a polymer solid state actuator.
Figure 13B:
FIG. 13b is a is a cross-section micrograph of a solid state actuator.

The new polymer solid-state actuator and sensor is fully dry, made with a composite of poly(ethylene oxide) (or its derivatives and similar ion-conducting solid-state materials) and poly(ethylene glycol), an effective plasticiser (or other plasticisers), in the form of a strip, which is then suitably surface-electroded and cation-doped. The constructed assembly of the actuator and sensor strip is composed of a 320 μm thickness of thin electrically conducting sheet being composed of a homogeneous form of poly(ethylene oxide) and poly(ethylene glycol) with a properly deposited (or composited) electrode. FIG. 13a shows a schematic of such actuator and sensor assembly and FIG. 13b shows an actuator along with its cross-sectional SEM micrograph. The micrograph of FIG. 13b shows a uniformly deposited metal layer (Pd and Au) at the outer surface of the actuator and sensor assembly. The mechanical strength can be improved by additives such as (tetrafluoroethylene) sulphonic acid. First, it should be noted that the reported polymer actuator exhibit large bending capabilities (>2% bending strain) at low electric field ($\vec{E}$<10$^1$ Vmm$^{-1}$) as can be seen in FIGS. 14a and 14b. The pictorial representations of FIGS. 14a and 14b show a polymer solid-state actuator with no voltage supplied in FIGS. 14a, and 14b shows the actuator with a static electric input of 9 volts ($\vec{E} \approx 30$ V/mm) applied. The actuator is a strip 5.0 mm wide and 70.2 mm long. Note in FIG. 6b that the strip bends towards the anode. The bending capability of this embodiment corresponds to a strain of approximately 1.5%. The time interval between FIG. 14a and FIG. 14b is 10 seconds. It should be noted that such electromechanical capabilities do not require interfacial dopant diffusion transport that is the usual necessity for conducting polymer actuators. Consequently, the polymer solid-state actuators shows fast responses and are highly efficient and operationally safe. Also, they are fully operational in dry environments for long-term operation.

Figure 15A:
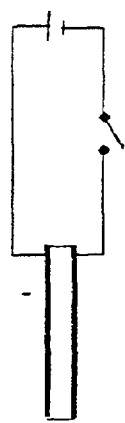
FIGS. 15a, 15b and 15c show the operating principle of the preferred polymer solid-state actuator.
Figure 15B:
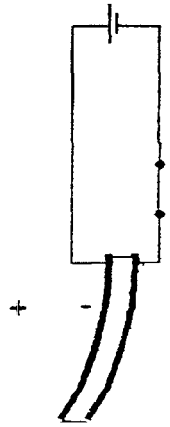
Figure 15C:
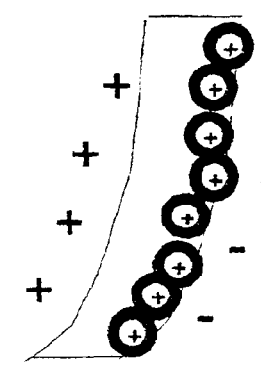

The operating principle of this new polymer solid-state actuator is depicted in FIGS. 15a, 15b and 15c. An equivalent electric field of approximately 30 V/mm Under an electric field, the actuator strip bends toward the anode due to redistributed doped ions via transient cross linking forcing the soft phase, poly(ethylene oxide), to be internally deformed and, therefore, the actuator assembly undergoes dynamic migration that can cause a local deformation of the material (one side expands and the other contracts). So, it oscillates in response to an alternating input voltage. An alternating current can trigger such an actuator to act like a flap wing that potentially mimics biological wing flaps or serve as large motion actuators/manipulators for robots.

Figure 16:
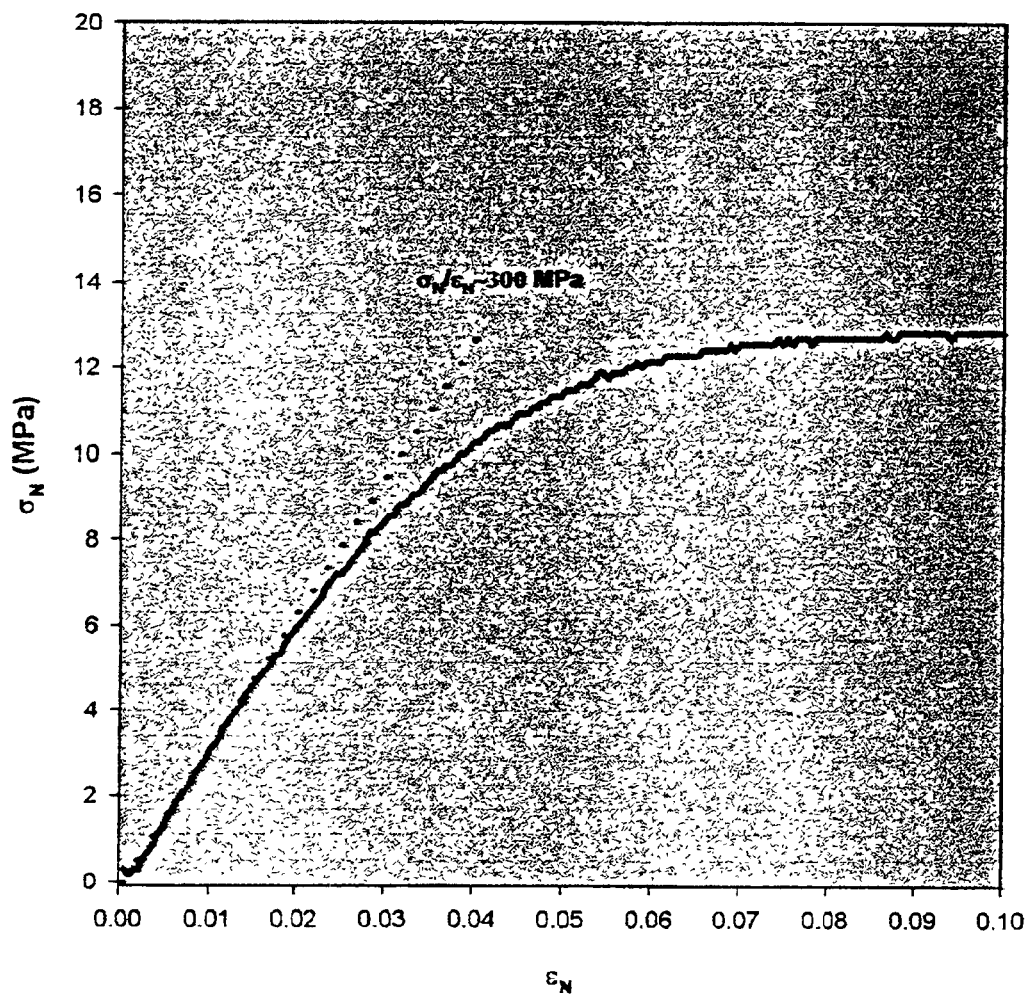
FIG. 16 is a graph showing the tensile testing results of the preferred polymer solid state actuator.
Figure 18:
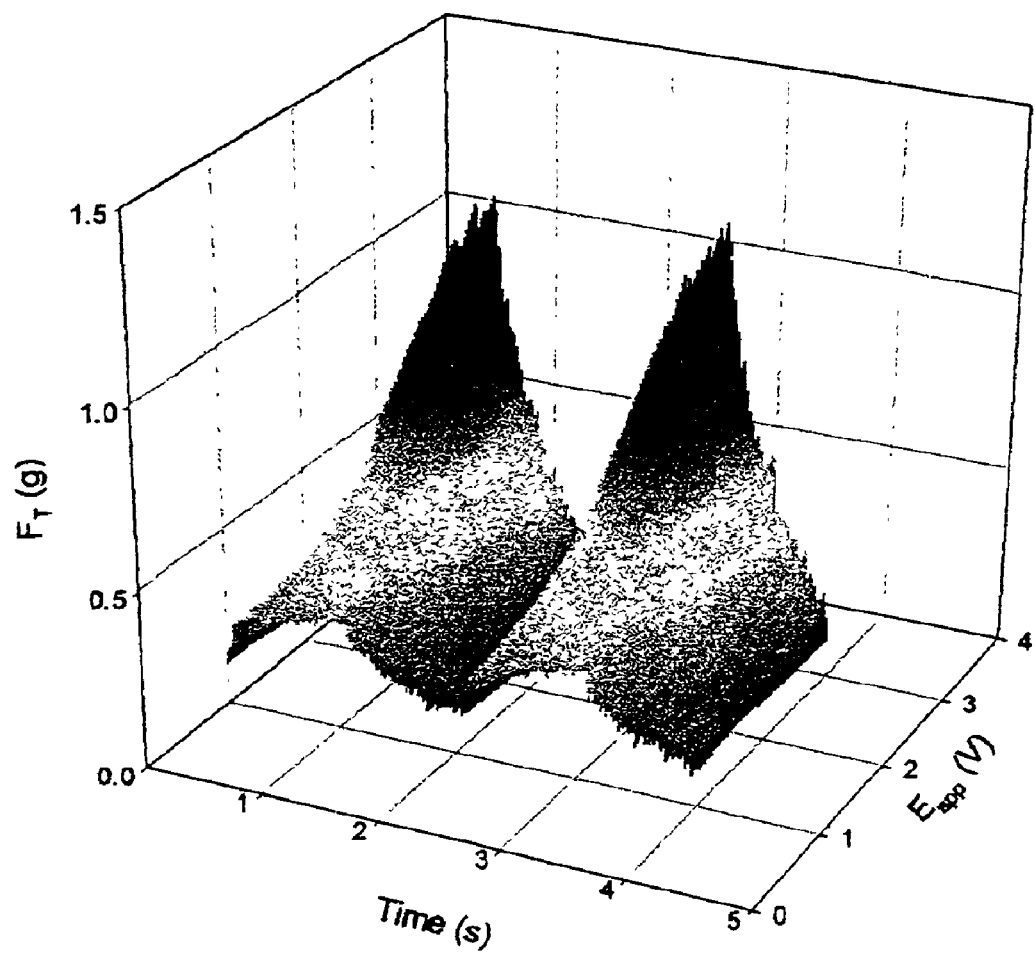
FIG. 18 is a graph of typical actuation responses of the preferred polymer solid-state actuator with a square wave input.
Figures 19A, 19B, 19C:
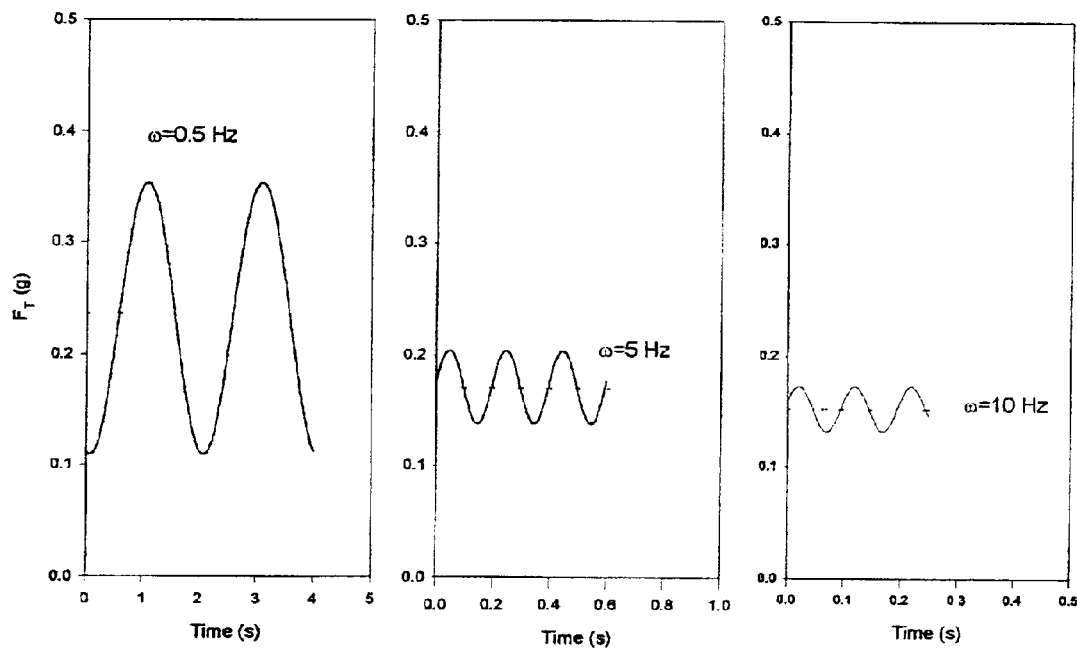
FIGS. 19a, 19b and 19c are graphs of typical actuation responses of the preferred manufactured polymer solid-state actuator for frequencies of 0.5, 5, and 10 Hz.
Figure 20:
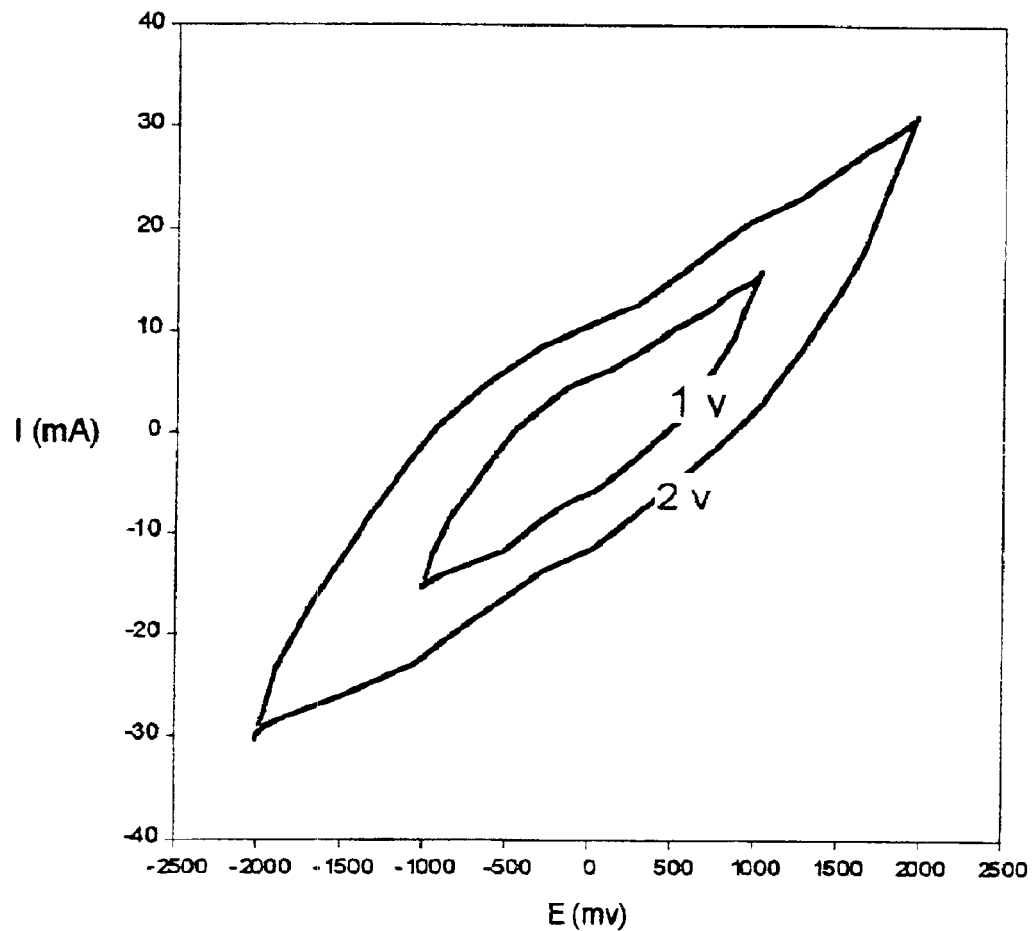
FIG. 20 is a graph of measured cyclic current/voltage of the preferred polymer solid-state actuator at a scan rate of 100 mV/sec.

The tensile strength of the manufactured polymer solid-state actuator and sensor material is shown in FIG. 16 in terms of the normal stress, $\sigma_N$, vs. normal strain, $\epsilon_N$, using a Instron table-top model 1011. The Young's modulus of this particular reported material at room temperature was approximately 300 MPa along with stress yielding at approximately 13 MPa. The load and force characteristics of the manufactured polymer solid-state actuator are briefly measured in a cantilever form using a load cell positioned at the tip of the cantilever, as shown in FIG. 17a. A PC based test platform was used for the actuation tests. A signal module conditioned a calibrated load cell. The manufactured polymer solid-state actuator sample was attached at one end to the load cell application point and the other placed at the contact electrode, which formed the jaws of a small circular contact having an area of approximately 3 mm². The tip forces generated against the gravity by a strip of the actuator were measured and are provided in FIGS. 17b, 17c, and 17d in which shows response characteristics at different sinusoidal input potentials of 1, 2, and 3 volts (top, middle, and bottom), respectively, maintaining a constant frequency of ½ Hz. The effective length and width of the sample actuator was 25.4 and 6.1 mm, respectively. The resulting graphs, FIGS. 17b, 17c, and 17d, were slightly pre-loaded and plotted over a 4 second period. This made the effective weight of the sample producing a useful force to be above 10 $g_{force}$/g of the polymer solid-state actuator within the appropriate voltage input. The data shows good force response characteristics of the polymer solid-state actuator with sinusoidal wave inputs of 1–3 volts. Similarly, the response characteristics to step voltages are also provided in FIG. 18. As expected, a small delayed response arising from ion movement was observed (not showing a sharp response to a step input voltage). In FIGS. 19a, 19b, and 19c the frequency response of the manufactured actuator at 0.5, 5, and 10 Hz, respectively, is shown. The graphs show reduced effective force generated as the frequency increases but overall showing good responses. In FIG. 20 a measured cyclic current/voltage of the actuator is provided (scan rate of 100 mV/sec). As can be seen, a rather simple behavior with small hysteresis is shown. The reactivity of poly(ethylene oxide) is mild in that it does not show any distinct reduction or re-oxidation peaks within +/−2 volts. Overall behavior shows the simple behavior of ionic motions caused under an imposed electric field.

Figure 21:
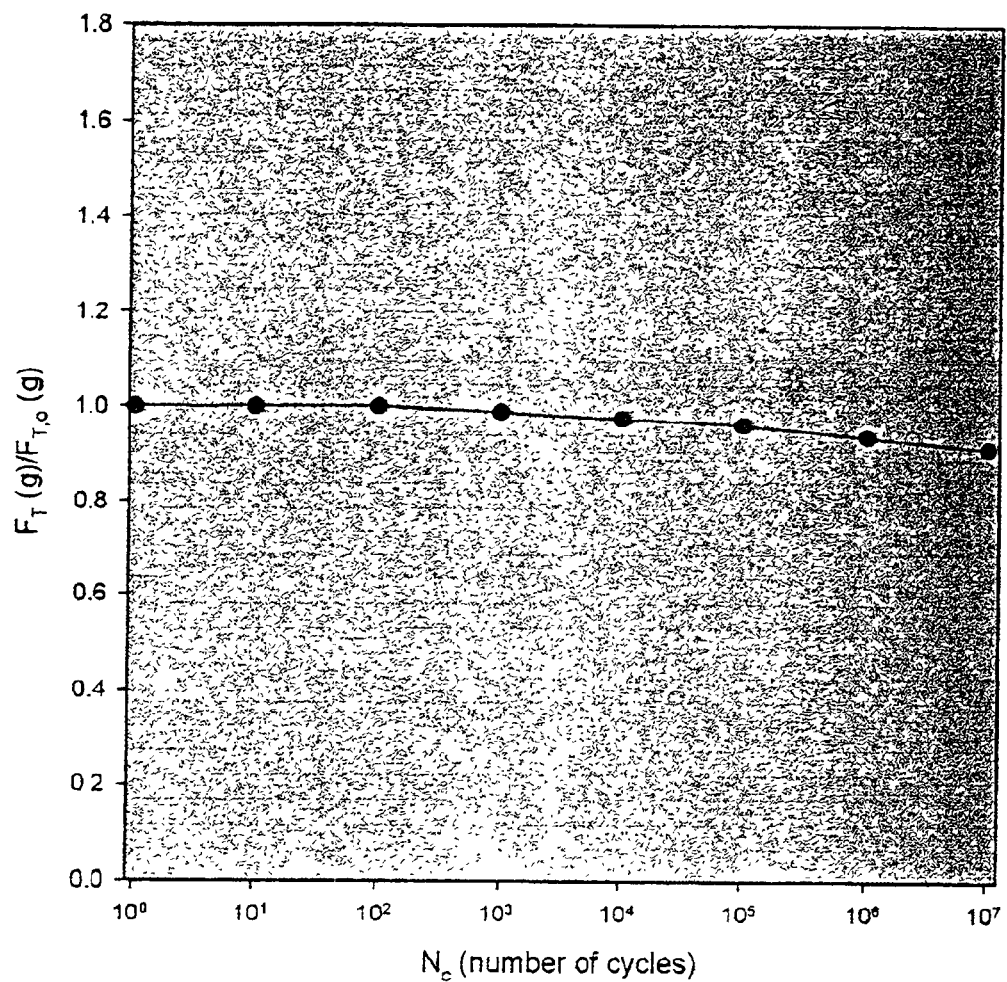
FIG. 21 is a graph showing test measurements of the preferred polymer solid-state actuator with a cyclical square wave input.

The longevity of the manufactured polymer solid-state actuators has been carefully tested and the results are shown in FIG. 21. It shows the measured tip force, $F_T$, against the number of cycles, $N_c$, at an imposed condition of 2 volts square wave signal and a frequency of 5 Hz. Please note that FTIP represents the tip force measured at the first cycle. No force degradation was observed up to 10 millions of cycles of oscillation under the square wave signal when the test was terminated. This finding indicates no irreversible actuation and sensing effect on the material and excellent long-term operational characteristics. This level of longevity is the first achievement in this category of materials including conducting polymers, ferroelectric polymers, ionic-polymer metal composites, and ionic polymer gels.

One way of describing the actuation and sensing principle of this polymer solid-state actuator and sensor is also possible based upon the linear irreversible thermodynamics; (with a current density, $J=\sigma\vec{E}-L_{12}\nabla p$) and internal soft-phase transport (with a flux, $Q=L_{21}\vec{E}-K\nabla p$). The conjugate forces include the electric field, $\vec{E}$, and the pressure gradient, $-\nabla p$. Important parameters include $\sigma$ and K, the material conductance and the permeability, respectively. A cross coefficient is usually $L_{12}=L_{21}=L$ that has a relevant meaning of the mobility of ions pushing and dragging the soft phase, poly(ethylene oxide), that in fact causes strain changes, under electric fields (L has a unit of $m^2$ $sec^{-1}$ $volt^{-1}$). Data shown in FIGS. 17, 18, and 19 can be translated into a cross coefficient, L, on the order of $10^{-8}$ $m^2$ $sec^{-1}$ $volt^{-1}$ that seems realistic.

It is well known that poly(ethylene oxide), previously recognized as a plastic electrolyte, is a linear polymer having a high degree of crystallinity due to lamellae structured as spherulites and allows effective ion-doping through a solvating polymer matrix via direct interaction of the cation (or cations) and electron pairs created by oxygen atoms, finally yielding a conductive solid-state polymer matrix. Such ionic conductivity within poly(ethylene oxide) is due to the existence of amorphous region. But, the use of plasticisers, such as poly(ethylene glycol), is known to decrease the crystallinity of the host medium leading to an increase in ion mobility due to improved miscibility with the amorphous region. Also, it is possible to incorporate the mechanical stability of poly(ethylene oxide) in the composite polymer when polymeric anions are introduced so as to create tight ionic forces while having a good conductivity. It should be pointed out that useful materials in this category of bending actuators examined so far include polymer electrolytes, polyelectrolytes, and gel electrolytes coordinated with small and large cations such as lithium, sodium, potassium, tetrabuthylammonim, and others (in the form of inorganic/or organic salts, lithium perchlorate, lithium trifluoromethanesulphonate, and sodium thiocyanate, and etc.).

Figure 22:
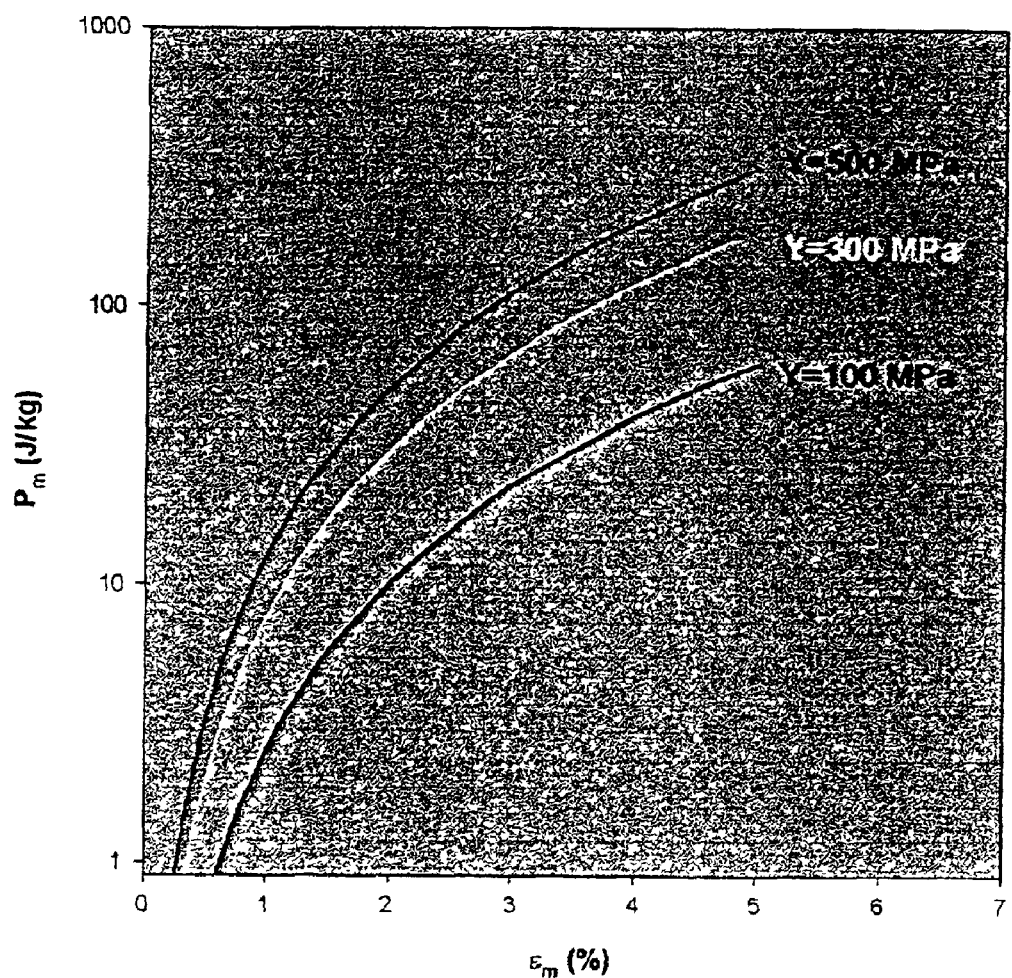
FIG. 22 depicts the strain-power density variations for the preferred polymer solid-sate actuator.

FIG. 22 depicts the strain-power density variations for the polymer solid-sate actuators. Moduli of 100, 300, and 500 MPa, are measured, respectively. The current effort producing 2% strain also produces the corresponding power densities, $P_m$, of 10, 30, and 50 J/kg, respectively, for the actuator. Further improvement of the polymer solid-state actuator will generate up to 4% strain and would lead to power densities of 40–200 J/kg, that is comparable to biological muscles. Furthermore, experimental investigations on the polymer solid-state actuators may be extended to determine deformation/maximum force, force/length relationship, power output, and fracture strength in a potential workspace of it.

As far as sensing capabilities of the invented polymer solid-state sensor, it can be seen in FIG. 11 where it shows the dynamic response of a strip of poly(ethylene oxide) and poly(ethylene glycol) subject to a dynamic impact loading as a cantilever form. A damped electric response is observed and was also highly repeatable with a high bandwidth up to $10^2$ Hz. Such direct mechanoelectric behaviors are related to the endo-ionic mobility due to imposed stresses. It means that, if we impose a finite soft-phase flux, $|Q|$, but not allowing a current flux, $J=0$, it creates a certain conjugate electric field, $\vec{E}$, that can be dynamically monitored. Also, the quasi-static response of the invented polymer solid-state sensor is provided in FIG. 12.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. A method of fabricating a dry electro-active polymeric synthetic muscle, the method comprising the steps of:
   a) providing a polyelectrolyte material;
   b) mixing the polyelectrolyte material with a conductive material; and
   c) affixing at least two electrodes to the mixed polyelectrolyte material and conductive material.

2. The method of claim 1 wherein the step of mixing comprises mixing a soluble polyelectrolyte material with an electrically conducting powder and drying the mixed polyelectrolyte material with the conductive material.

3. The method of claim 1 wherein the step of mixing comprises combining a dry polyelectrolyte material with a dry conductive material and applying heat to the combined materials.

4. The method of claim 1 wherein the step of mixing comprises combining a dry polyelectrolyte material with a dry conductive material and applying pressure to the combined materials.

5. The method of claim 1 wherein the step of affixing at least two electrodes comprises penetrating the at least two electrodes into the mixed polyelectrolyte material and conductive material.

6. The method of claim 5 wherein the step of penetrating the at least two electrodes into the mixed polyelectrolyte material and conductive material comprises heating the penetrated at least two electrodes and the mixed polyelectrolyte material and conductive material.

7. The method of claim 5 wherein the step of penetrating the at least two electrodes into the mixed polyelectrolyte material and conductive material comprises pressurizing the penetrated at least two electrodes and the mixed polyelectrolyte material and conductive material.

8. The method of claim 1 wherein the step of affixing at least two electrodes comprises physical loading and interlocking primary electrically conducting particles with smaller electrically conducting particles within the polyelectrolyte material.

9. The method of claim 1 wherein the polyelectrolyte material comprises a member from the group consisting of polyethylene oxide, polyethylene succinate, polypropiolactone, polyethylene adipate, polypropylene oxide, polymethacrylic acid, polyacrylonitrile, polybismethoxyethoxyethoxy phosphazene and polyvinylidene fluoride.

10. The method of claim 1 wherein the synthetic muscle comprises a sensing device.

11. The method of claim 1 wherein the synthetic muscle comprises a transducing device.

12. The method of claim 1 wherein the synthetic muscle comprises an actuating device.

* * * * *